(12) United States Patent
Jezierski

(10) Patent No.: US 9,855,069 B2
(45) Date of Patent: Jan. 2, 2018

(54) MAGNETIC COUPLING MOTOR DRIVE FOR SURGICAL CUTTING INSTRUMENT

(71) Applicant: Smith & Nephew, Inc., Memphis, TN (US)

(72) Inventor: Rafal Z. Jezierski, Middleton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 356 days.

(21) Appl. No.: 14/483,239

(22) Filed: Sep. 11, 2014

(65) Prior Publication Data

US 2016/0074057 A1   Mar. 17, 2016

(51) Int. Cl.
*A61B 17/32* (2006.01)
*A61B 17/00* (2006.01)
*A61B 17/16* (2006.01)

(52) U.S. Cl.
CPC .... *A61B 17/32002* (2013.01); *A61B 17/1624* (2013.01); *A61B 2017/0046* (2013.01); *A61B 2017/00398* (2013.01); *A61B 2017/00477* (2013.01); *A61B 2017/00876* (2013.01); *A61B 2017/320032* (2013.01)

(58) Field of Classification Search
CPC ....... A61B 2017/320024; A61B 2017/320028; A61B 2017/320032; A61B 2017/00398; A61B 2017/00411; A61B 2017/00415; A61B 2017/00477; A61B 2017/00486; A61B 2017/0046; A61B 2017/00876; A61B 17/32002; A61B 17/320016; H02K 49/104; H02K 49/106; H02K 49/108; H02K 5/165

See application file for complete search history.

(56) References Cited

U.S. PATENT DOCUMENTS

| | | | |
|---|---|---|---|
| 4,486,176 A | 12/1984 | Tardieu et al. | |
| 5,204,572 A * | 4/1993 | Ferreira | H02K 49/106 310/156.19 |
| 5,569,179 A | 10/1996 | Adrian | |
| 2008/0234714 A1* | 9/2008 | Jezierski | A61B 17/32002 606/170 |
| 2010/0217245 A1* | 8/2010 | Prescott | A61B 17/32002 606/1 |

FOREIGN PATENT DOCUMENTS

WO   2014/081661 A1   5/2014

OTHER PUBLICATIONS

Search Report, PCT/US2015/049060, dated Nov. 11, 2015, pp. 5.

* cited by examiner

*Primary Examiner* — Jocelin Tanner

(57) ABSTRACT

Apparatus and methods for a magnetic coupling motor drive for a surgical cutting instrument. A magnetic coupling motor drive unit includes a motor housing containing a motor and a magnetic drive hub assembly, the magnetic drive hub assembly having a drive hub and a driven hub, the driven hub rotating about a driven hub spindle, the driven hub spindle attached to a seal cap, the seal cap sealing the drive hub and the motor to the motor housing, wherein the drive hub includes an array of magnets aligned to a respective array of magnets in the driven hub.

19 Claims, 4 Drawing Sheets

MAGNETIC COUPLING MOTOR DRIVE FOR SURGICAL CUTTING INSTRUMENT

BACKGROUND OF THE INVENTION

The present invention generally relates to cutting tools, and more particularly to a magnetic coupling motor drive for a surgical cutting instrument.

Arthroscopic instruments can be used to cut tissue mechanically in various parts of a body, such as, for example, a knee, using a blade that is rotated, or otherwise brought into contact with the tissue to be cut. These tools generally include a rotary blade driven by a motor drive. A drive adapter, which connects the motor drive to the blade, is directly attached to the motor output shaft. Conventional motor drive units typically utilize a radial seal to prevent ingress of contaminants into the motor housing at the interface between the motor output shaft and the housing. However, this arrangement can be difficult to clean, and serviceability of the motor drive unit may be impaired, potentially reducing the lifetime of the unit.

Accordingly, a device having improved cleanability and service life is desirable.

SUMMARY OF THE INVENTION

The present invention is directed towards a magnetic coupling motor drive for a surgical cutting instrument.

In an aspect, the invention features an apparatus including a blade assembly including an elongate outer tubular member having a distal opening, an elongate inner tubular member coaxially disposed within the elongate outer tubular member and including a cutting element aligned with the distal opening of the outer tubular member, a magnetic coupling motor drive unit, the magnetic coupling motor drive unit coupled to a proximal end of the elongate outer tubular member and a proximal end of the elongate inner tubular member, the magnetic coupling motor drive unit rotating the elongate inner tubular member relative to the elongate outer tubular member, and the magnetic coupling motor drive unit including a motor housing containing a motor and a magnetic drive hub assembly, the magnetic drive hub assembly including a drive hub and a driven hub, the driven hub rotating about a driven hub spindle, the driven hub spindle attached to a seal cap, the seal cap sealing the drive hub and the motor to the motor housing.

One or more of the following features may also be included.

A distal end of the elongate inner tubular member may have a surface for engaging tissue via the distal opening of the elongate outer tubular member to shear or cut tissue.

The driven hub spindle may be located in a center of the seal cap, positioning the driven hub axially and radially with respect to the drive hub.

The drive hub can include an array of magnets aligned to a respective array of magnets in the driven hub. The magnet alignment can be axial or radial.

The drive hub can be magnetically coupled to the driven hub across an air gap containing a wall of the seal cap.

The apparatus may include a blade drive fork attached to the driven hub, the blade drive fork providing a rotational force to the elongate inner tubular member.

The seal cap may be non-metal non-conductive material.

In another aspect, the invention features a magnetic coupling motor drive unit including a motor housing containing a motor and a magnetic drive hub assembly, the magnetic drive hub assembly including a drive hub and a driven hub, the driven hub rotating about a driven hub spindle, the driven hub spindle attached to a seal cap, the seal cap sealing the drive hub and the motor to the motor housing, wherein the drive hub includes an array of magnets aligned to a respective array of magnets in the driven hub.

One or more of the following features may also be included.

The driven hub spindle can be located in a center of the seal cap, positioning the driven hub axially and radially with respect to the drive hub.

The magnet alignment can be axial or radial.

The drive hub can be magnetically coupled to the driven hub across an air gap containing a wall of the seal cap.

The apparatus may include a blade drive fork attached to the driven hub, the blade drive fork providing a rotational force to the elongate inner tubular member.

The seal cap may be non-metal non-conductive material.

In another aspect, the invention features a method for using a surgical cutting instrument, the method including providing a motor contained in a motor drive unit housing, providing a drive hub assembly, the drive hub assembly including a drive hub and a driven hub, the driven hub rotating about a driven hub spindle, the drive hub including an array of magnets aligned to a respective array of magnets in the driven hub, linking the motor drive unit to the drive hub assembly with an output shaft, linking the drive hub assembly to an elongate member with the driven hub spindle, and rotating the elongate member.

In another aspect, the invention features an apparatus including a tubular structure, and a magnetic coupling motor drive unit adapted to rotate the tubular structure, the magnetic coupling motor drive unit including a motor housing containing a motor and a magnetic drive hub assembly, the magnetic drive hub assembly including a drive hub and a driven hub, the driven hub rotating about a driven hub spindle, the driven hub spindle attached to a seal cap, the seal cap sealing the drive hub and the motor to the motor housing, wherein the drive hub includes an array of magnets aligned to a respective array of magnets in the driven hub.

Embodiments of the invention may include one or more of the following advantages.

The magnetic coupling motor drive of the present invention eliminates a motor drive output shaft radial seal, which is a major contributor to motor device unit (MDU) field failures and customer returns.

The driven hub assembly of the present invention is easily removed for improved access during cleaning/sterilization.

The magnetic coupling of the present invention protects the motor drive from damage due to excessive impact loads enabling the driven hub to slip relative to the drive hub once a maximum torque limit is reached.

The magnetic coupling motor drive of the present invention enables deployment of a modular attachment system to adapt the MDU to other powered instrument applications.

The magnetic coupling motor drive of the present invention enables easy replacement of the driven hub by an end-user in case of damage.

The magnetic coupling motor drive of the present invention reduces vibration in a surgical cutting instrument.

The magnetic coupling motor drive of the present invention reduces a need for perfect alignment of the drive hub and the driven hub due to a tendency of the subassemblies to realign based on attractive and repulsive force balance.

The magnetic coupling motor drive of the present invention reduces contact between moving parts. Instead of direct contact, there is an air gap between the motor and the load it is driving. This reduces friction and can increase the efficiency. It also reduces wear and tear on the motor, which may increase its life.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The invention will be more fully understood by reference to the detailed description, in conjunction with the following figures, wherein.

DETAILED DESCRIPTION

Figure 1:
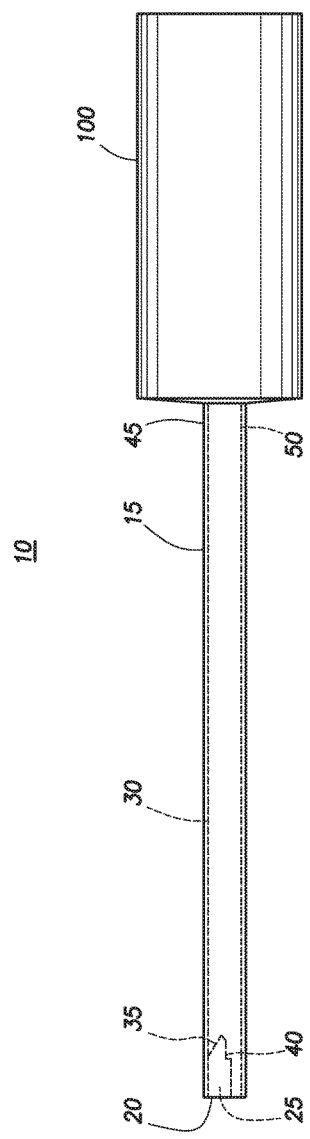
FIG. 1 is an illustration of an exemplary surgical cutting instrument.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the term "or" is intended to mean an inclusive "or" rather than an exclusive "or." That is, unless specified otherwise, or clear from context, "X employs A or B" is intended to mean any of the natural inclusive permutations. That is, if X employs A, X employs B, or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Although the present invention is described for a surgical cutting instrument, it may be suitable for, or adapted for, use in other powered instruments.

As shown in FIG. 1, an exemplary surgical cutting instrument 10 for use in arthroscopic surgery includes an elongate outer tubular member 15 terminating at a distal end 20 having an opening 25 in a side wall and/or an end wall to form a cutting port or window, and an elongate inner tubular member 30 coaxially disposed, and rotatable within the elongate outer tubular member 15 and having a distal end 35 disposed adjacent the opening 25 in the distal end 20 of the elongate outer tubular member 15.

The distal end 35 of the elongate inner tubular member 30 has a surface or edge 40 for engaging tissue via the opening 25 in the distal end 20 of the elongate outer tubular member 15 and cooperates with the opening 25 to shear or cut tissue. A vacuum source (not shown) may be coupled to the surgical cutting instrument 10 and aspirates cut tissue, and the irrigating fluid surrounding the tissue, from the surgical cutting instrument 10.

A proximal end 45 of the elongate outer tubular member 15 and a proximal end 50 of the elongate inner tubular member 30 are linked to an exemplary magnetic coupling motor drive unit 100. The magnetic motor drive unit 100 rotates the elongate inner tubular member 30 within the stationary elongate outer tubular member 15 using finger-actuated switches on a hand piece (not shown). Power (not shown) to the motor drive unit 100 may be AC/DC or one or more batteries.

Figure 2:
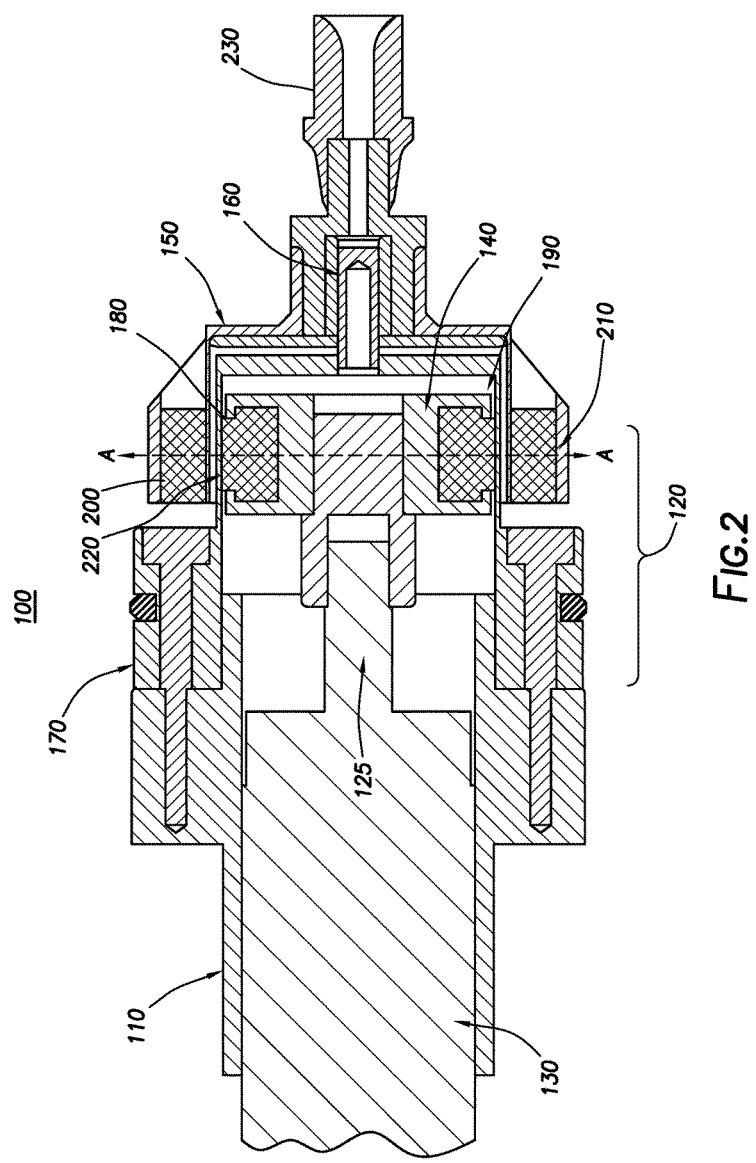
FIG. 2 is an illustration of a cross section of a first exemplary magnetic coupling motor drive unit of surgical cutting instrument of FIG. 1.

As shown in FIG. 2, the exemplary magnetic coupling motor drive unit 100 includes a motor housing 110 and a magnetic drive hub assembly 120. The motor housing 110 includes a motor 130. The motor housing 110 is linked to the magnetic drive hub assembly 120 by an output shaft 125.

The magnetic drive hub assembly 120 includes a drive hub 140 and a driven hub 150. The driven hub 150 rotates about a driven hub spindle 160. The driven hub spindle 160 is attached to a seal cap 170. The seal cap 170 seals the drive hub 140 and the motor 130 to the motor housing 110. In embodiments, the seal cap 170 is a non-metal non-conductive material. The driven hub spindle 160 is located in a center of the seal cap 170, positioning the driven hub 150 axially and radially with respect to the drive hub 140.

The drive hub 140 includes an array of magnets 180, 190, radially aligned to a respective array of magnets 200, 210 in the driven hub 150.

The drive hub 140 is magnetically coupled to the driven hub 150 across an air gap 220 containing a wall of the seal cap 170. A direction of magnetism for the radial array of alternating polarity magnets 180, 190, 200, 210 is shown along an axis A-A. A movement of drive hub 140 provides the magnetic force to turn the driven hub 150.

A blade drive fork 230 is attached to the driven hub 150. The blade drive fork 230 provides rotational force to the elongate inner tubular member 30 (of FIG. 1).

Although the magnets 180, 190, 200, 210 are shown in an array arranged in a radial direction, alternate embodiments of the magnetic drive hub assembly 120 can include, for example, the number, geometry and size of the magnets within the array, an axial or radial direction of the array magnetism, a nesting (radial) alignment of magnet arrays, and a parallel (axial) alignment of magnet arrays.

Figure 3:
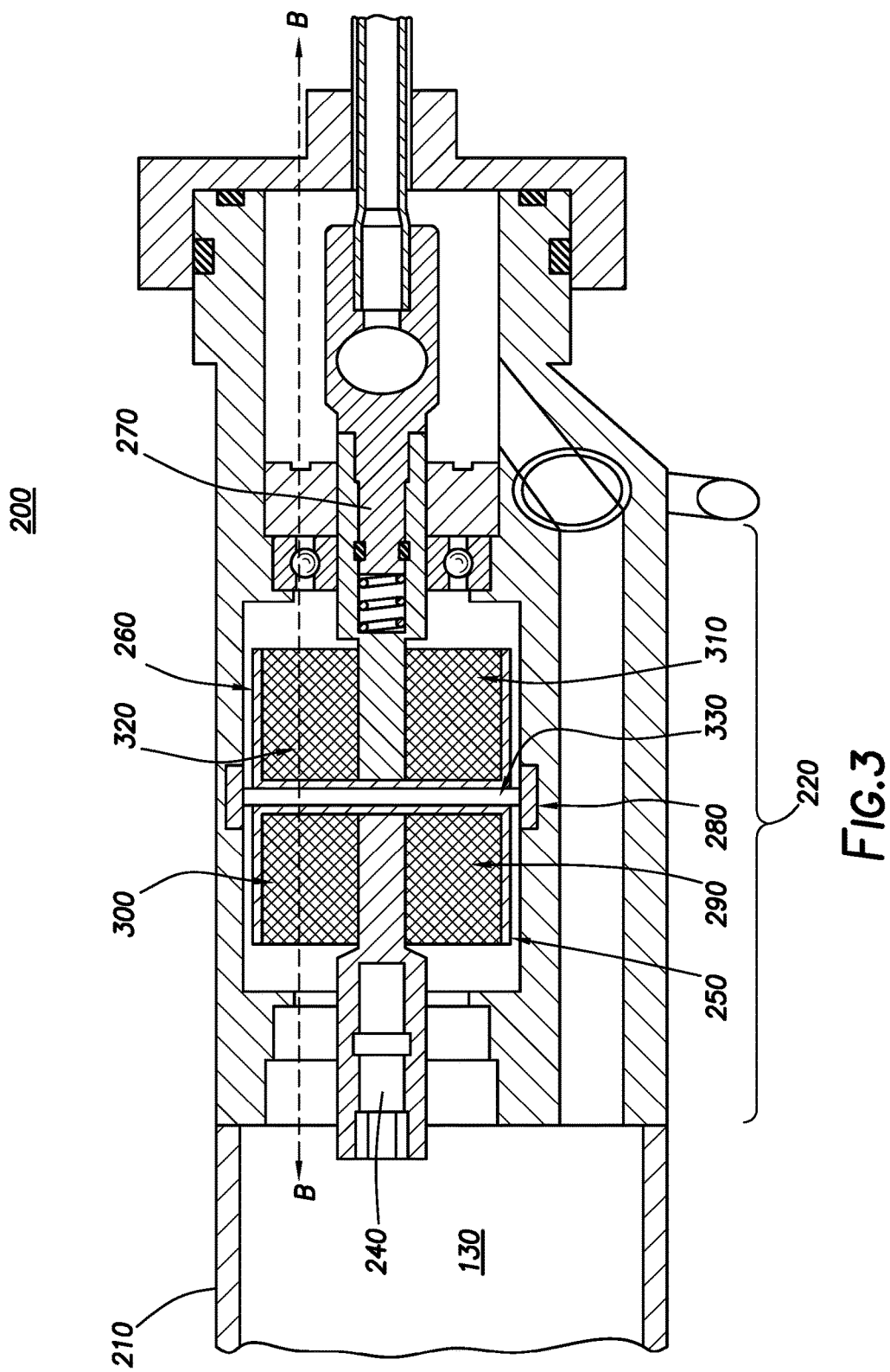
FIG. 3 is an illustration of cross section of a second exemplary magnetic coupling motor drive unit of surgical cutting instrument FIG. 1.

As shown in FIG. 3, a cross section of a second embodiment of an exemplary magnetic coupling motor drive unit (MDU) 200 includes a motor housing 210 and a magnetic drive hub assembly 220. The motor housing 210 includes a motor 130. The motor housing 210 is linked to the magnetic drive hub assembly 220 by an output shaft 240.

The magnetic drive hub assembly 220 includes a drive hub 250 and a driven hub 260. The driven hub 260 rotates about a driven hub spindle 270. A seal cap 280 seals the drive hub 250 and the driven hub 260. In embodiments, the seal cap 280 is a non-metal non-conductive material.

The drive hub 250 includes an array of magnets 290, 300 axially aligned to a respective array of magnets 310, 320 in the driven hub 260.

The drive hub 250 is magnetically coupled to the driven hub 260 across an air gap 330 containing a wall of the seal cap 280. A direction of magnetism for the axial array of alternating polarity magnets 290, 300, 310, 320 is shown along an axis B-B. A movement of drive hub 250 provides the magnetic force to turn the driven hub 260.

A blade drive fork 230 is attached to the driven hub 260. The blade drive fork 230 provides rotational force to the elongate inner tubular member 30 (of FIG. 1).

Figure 4:
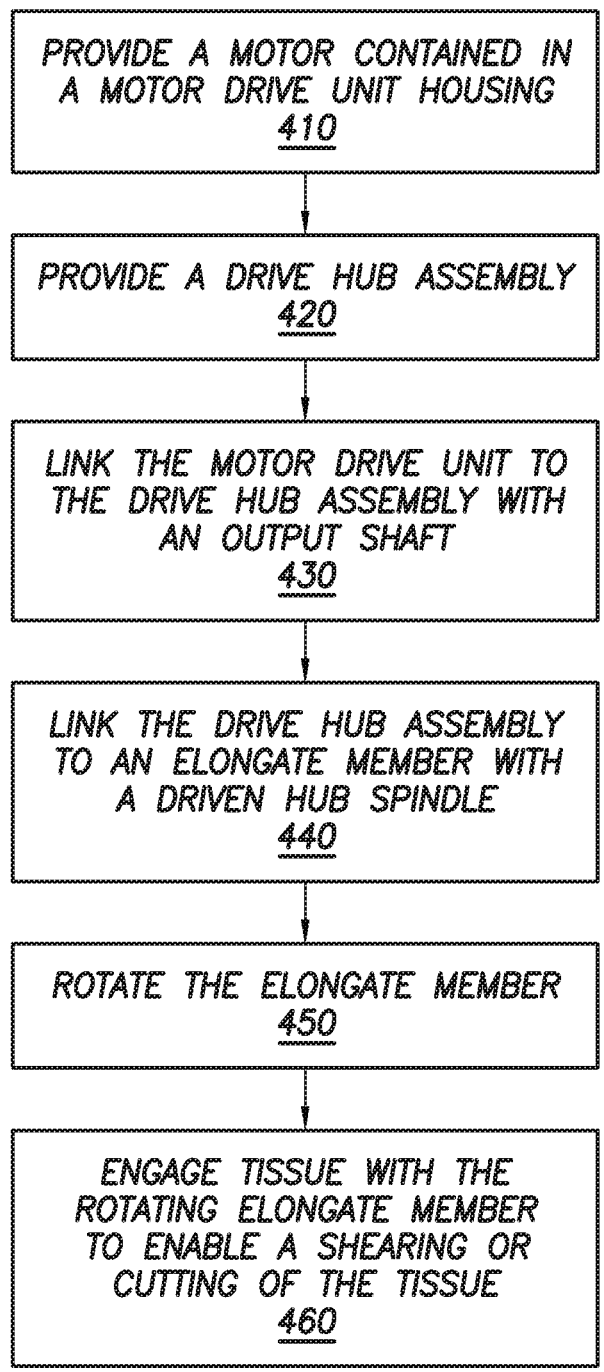
FIG. 4 is a flow diagram.

As shown in FIG. 4, a process 400 for using a surgical cutting instrument includes providing (410) a motor contained in a motor drive unit housing.

Process 400 includes providing (420) a drive hub assembly. The drive hub assembly includes a drive hub and a driven hub. The drive hub is magnetically coupled to the driven hub across an air gap containing a wall of a seal cap.

The process 400 links (430) the motor drive unit to the drive hub assembly with an output shaft and links (440) the drive hub assembly to an elongate member with a driven hub spindle.

Process 400 rotates (450) the elongate member and engages (460) tissue with the rotating elongate member to enable a shearing or cutting of the tissue.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

What is claimed is:

1. An apparatus comprising:
   a blade assembly comprising an elongate outer tubular member having a distal opening;
   an elongate inner tubular member coaxially disposed within the elongate outer tubular member and comprising a cutting element aligned with the distal opening of the outer tubular member;
   a magnetic coupling motor drive unit, the magnetic coupling motor drive unit coupled to a proximal end of the elongate outer tubular member and a proximal end of the elongate inner tubular member, the magnetic coupling motor drive unit configured to rotate the elongate inner tubular member relative to the elongate outer tubular member; and
   the magnetic coupling motor drive unit comprising a motor housing containing a motor and a magnetic drive hub assembly, the magnetic drive hub assembly comprising a drive hub and a driven hub, the driven hub configured to rotate about a driven hub spindle, the driven hub spindle attached to a seal cap, the seal cap seals the drive hub and the motor to the motor housing; and
   the driven hub spindle is located in a center of the seal cap, and the drive hub spindle configured to position the driven hub axially and radially with respect to the drive hub.

2. The apparatus of claim 1 wherein a distal end of the elongate inner tubular member has a surface for engaging tissue via the distal opening of the elongate outer tubular member to shear or cut tissue.

3. The apparatus of claim 1 wherein the drive hub comprises an array of magnets aligned to a respective array of magnets in the driven hub.

4. The apparatus of claim 3 wherein the magnet alignment is axial.

5. The apparatus of claim 3 wherein the magnet alignment is radial.

6. The apparatus of claim 3 wherein the drive hub is magnetically coupled to the driven hub across an air gap containing a wall of the seal cap.

7. The apparatus of claim 1 wherein the seal cap is non-metal non-conductive material.

8. An apparatus comprising:
   a blade assembly comprising an elongate outer tubular member having a distal opening;
   an elongate inner tubular member coaxially disposed within the elongate outer tubular member and comprising a cutting element aligned with the distal opening of the outer tubular member;
   a magnetic coupling motor drive unit, the magnetic coupling motor drive unit coupled to a proximal end of the elongate outer tubular member and a proximal end of the elongate inner tubular member, the magnetic coupling motor drive unit configured to rotate the elongate inner tubular member relative to the elongate outer tubular member; and
   the magnetic coupling motor drive unit comprising a motor housing containing a motor and a magnetic drive hub assembly, the magnetic drive hub assembly comprising a drive hub and a driven hub, the driven hub configured to rotate about a driven hub spindle, the driven hub spindle attached to a seal cap, the seal cap seals the drive hub and the motor to the motor housing;
   a blade drive fork attached to the driven hub, the blade drive fork configured to provide a rotational force to the elongate inner tubular member.

9. A magnetic coupling motor drive unit comprising:
   a motor housing containing a motor and a magnetic drive hub assembly, the magnetic drive hub assembly comprising a drive hub and a driven hub, the driven hub configured to rotate about a driven hub spindle, the driven hub spindle attached to a seal cap, the seal cap sealing the drive hub and the motor to the motor housing, wherein the drive hub comprises an array of magnets aligned to a respective array of magnets in the driven hub;
   the driven hub spindle is located in a center of the seal cap, and the drive hub spindle configured to position the driven hub axially and radially with respect to the drive hub.

10. The apparatus of claim 9 wherein the drive hub is magnetically coupled to the driven hub across an air gap containing a wall of the seal cap.

11. The apparatus of claim 9 wherein the seal cap is non-metal non-conductive material.

12. A magnetic coupling motor drive unit comprising:
   a motor housing containing a motor and a magnetic drive hub assembly, the magnetic drive hub assembly comprising a drive hub and a driven hub, the driven hub configured to rotate about a driven hub spindle, the driven hub spindle attached to a seal cap, the seal cap seals the drive hub and the motor to the motor housing, wherein the drive hub comprises an array of magnets aligned to a respective array of magnets in the driven hub;
   a blade drive fork attached to the driven hub, the blade drive fork configured to provide a rotational force to an elongate inner tubular member.

13. The apparatus of claim 12 wherein the magnet alignment is axial.

14. The apparatus of claim 12 wherein the magnet alignment is radial.

15. An apparatus comprising:
   a tubular structure; and a magnetic coupling motor drive unit adapted to rotate the tubular structure, the magnetic coupling motor drive unit comprising a motor housing containing a motor and a magnetic drive hub assembly, the magnetic drive hub assembly comprising a drive hub and a driven hub, the driven hub configured to rotate about a driven hub spindle, the driven hub spindle attached to a seal cap, the seal cap seals the drive hub and the motor to the motor housing, wherein the drive hub comprises an array of magnets aligned to a respective array of magnets in the driven hub;

the driven hub spindle is located in a center of the seal cap, the driven hub spindle configured to position the driven hub axially and radially with respect to the drive hub.

16. The apparatus of claim 15 wherein the magnet alignment is axial.

17. The apparatus of claim 15 wherein the magnet alignment is radial.

18. The apparatus of claim 15 wherein the drive hub is magnetically coupled to the driven hub across an air gap containing a wall of the seal cap.

19. An apparatus comprising:
a tubular structure; and
a magnetic coupling motor drive unit adapted to rotate the tubular structure, the magnetic coupling motor drive unit comprising a motor housing containing a motor and a magnetic drive hub assembly, the magnetic drive hub assembly comprising a drive hub and a driven hub, the driven hub configured to rotate about a driven hub spindle, the driven hub spindle attached to a seal cap, the seal cap seals the drive hub and the motor to the motor housing, wherein the drive hub comprises an array of magnets aligned to a respective array of magnets in the driven hub;
a blade drive fork attached to the driven hub, the blade drive fork configured to provide a rotational force to the tubular structure.

\* \* \* \* \*